United States Patent [19]

Kesling

[11] Patent Number: 5,017,132

[45] Date of Patent: May 21, 1991

[54] INDIVIDUAL ROOT TORQUING AUXILIARY

[75] Inventor: Christopher K. Kesling, LaPorte, Ind.

[73] Assignee: TP Orthodontics, Inc., Westville, Ind.

[21] Appl. No.: 494,616

[22] Filed: Mar. 16, 1990

[51] Int. Cl.$^5$ .............................................. A61C 3/00
[52] U.S. Cl. ........................................ 433/18; 433/21
[58] Field of Search .................................... 433/18, 21

[56] References Cited

U.S. PATENT DOCUMENTS

| | | | |
|---|---|---|---|
| 3,256,602 | 6/1966 | Broussard et al. | 433/21 X |
| 3,762,050 | 10/1973 | Dal Pont | 433/21 |
| 4,354,834 | 10/1982 | Wilson | 433/21 |
| 4,580,976 | 4/1986 | O'Meara | 433/21 |
| 4,676,747 | 6/1987 | Kesling | 433/18 |
| 4,842,514 | 6/1989 | Kesling | 433/21 |
| 4,897,036 | 1/1990 | Kesling | 433/18 |

Primary Examiner—Robert P. Swiatek
Assistant Examiner—Nicholas D. Lucchesi
Attorney, Agent, or Firm—Lloyd L. Zickert

[57] ABSTRACT

An individual root torquing auxiliary for use with an edgewise bracket having a vertical slot which includes a torquing arm received in the vertical slot and a tail for engagement in the archwire slot of one or more adjacent brackets, wherein the axis of torquing is centered substantially along the main archwire.

16 Claims, 1 Drawing Sheet

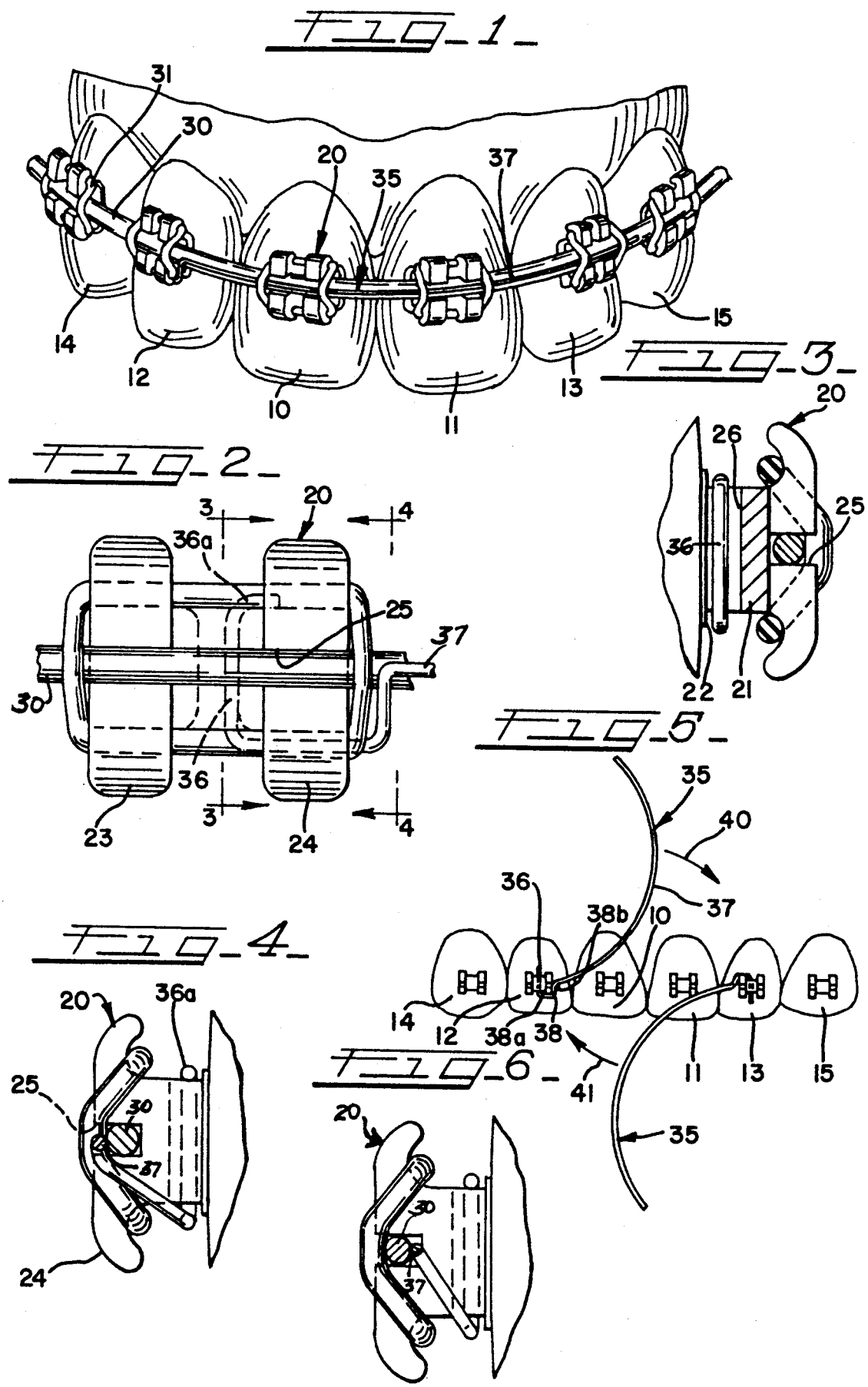

INDIVIDUAL ROOT TORQUING AUXILIARY

DESCRIPTION

This invention relates in general to an individual root torquing auxiliary for use with edgewise brackets having a vertical slot, and more particularly to an individual root torquing auxiliary for applying root torquing forces lingually or labially, and still more particularly to an individual root torquing auxiliary for use with an edgewise bracket having a vertical slot to apply a torquing force to a single tooth.

BACKGROUND OF THE INVENTION

Heretofore, root torquing auxiliaries have been anchored in an archwire slot and provided with loops between the brackets or on either side of a bracket in order to apply a root torquing force to a single tooth. Such auxiliaries are bulky for use with edgewise brackets and contribute to difficulties in maintaining good oral hygiene. Moreover, such auxiliaries have been unsightly and noticeable.

SUMMARY OF THE INVENTION

The individual root torquing auxiliaries of the present invention obviates the above difficulties in providing a unique auxiliary for torquing the root of a single tooth in an edgewise technique case where edgewise brackets are used with vertical slots. The auxiliary of the invention includes a torquing arm that is received in the vertical slot and may be anchored to the bracket by bending over the end of the arm against the bracket, and a tail or lever arm serving as the activating member which is to be anchored in the main archwire slot of one or more adjacent brackets. The tail is preferably inserted first into the archwire slot ahead of the main archwire. The torquing arm end of the auxiliary is formed so that it is connected to the tail at the level of the archwire slots so that the tail is completely hidden behind the main archwire when inserted before the main archwire is inserted. The auxiliary may be used without modification to apply lingual or labial root torquing forces, depending on whether the torquing arm is inserted in the vertical slot from the incisal or the gingival. By virtue of the tail being at the level of the main archwire slot, the torquing axis is centered along the main archwire. By the tail being generally hidden behind the main archwire, improved aesthetics and better oral hygiene are produced. The auxiliary is not bulky and therefore it is easy to use.

An object of the present invention is in the provision of a new and improved root torquing auxiliary for use with edgewise brackets having vertical slots and which produces improved aesthetics and better oral hygiene.

Another object of the invention is in the provision of an individual root torquing auxiliary having a torquing arm insertable in the vertical slot of an edgewise bracket and a tail or lever arm that is anchored in the main archwire slot of one or more brackets, wherein the tail is positioned to be essentially hidden behind the main archwire to improve the visual appearance of a person.

Another object of the present invention is in the provision of an individual root torquing auxiliary for use with edgewise brackets having vertical slots and which is easy to use and economical to manufacture and which applies the torquing force to the tooth directly through the bracket.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a fragmentary elevational view of anterior teeth having edgewise brackets mounted thereon and including a main archwire in the archwire slot together with a torquing auxiliary according to the invention for applying torque to a single tooth;

FIG. 2 is a greatly enlarged front elevational view of the bracket on the tooth to be torqued and illustrating the anchoring of the torquing arm of the auxiliary to the bracket;

FIG. 3 is a vertical sectional view taken substantially along line 3—3 of FIG. 2;

FIG. 4 is a sectional view of the archwire and auxiliary and looking at the mesial side of the bracket substantially along line 4—4 of FIG. 2;

FIG. 5 is a front layout of the anterior teeth with edgewise brackets mounted thereon in schematic for illustrating the installation of the torquing auxiliary of the invention to provide lingual or labial torquing; and FIG. 6 is a view similar to FIG. 4 with the exception that the tail or lever arm of the auxiliary is shown positioned behind the main archwire.

DESCRIPTION OF THE INVENTION

Referring now to the drawing, and particularly to FIG. 1, anterior teeth are illustrated which include centrals 10 and 11, laterals 12 and 13, and canines 14 and 15, each of which has mounted thereon an edgewise bracket 20. Each edgewise bracket 20 includes a base 21 mounted on a bonding pad 22 that is in turn suitably bonded to the labial face of the tooth. Spaced apart tie wings 23 and 24 extend from the base. Each of the tie wings is provided with a horizontally extending and labially opening archwire slot, which slots are collectively indicated at 25. A vertical slot 26 is defined in the base for purposes of receiving an auxiliary. It will be appreciated that the bracket illustrated is a twin tie wing bracket of the standard type, although the present invention may be used with other types of edgewise brackets that may have single or twin tie wings as long as they have a vertical slot.

A main archwire 30 is received in the archwire slots and suitably ligated thereto by elastic ligatures 31. It will be appreciated that metal ligatures may be used if so desired. The archwire 30 is round although it may be appreciated that an undersized rectangular wire may be provided when it is desired to torque a tooth. Preferably, a round archwire is used as illustrated as torquing is accomplished about the axis of the main archwire.

The torquing auxiliary of the invention is illustrated in its unstressed or passive state in FIG. 5 and in its activated state in FIG. 1. The torquing auxiliary includes a torquing arm 36, a tail or lever arm 37, and a connecting member 38. The torquing arm 36 engages in the vertical slot of the bracket on the tooth to be torqued and is of a length to extend through the vertical slot and be bent over the bracket to lock it in place, as shown by the bent over end 36a in FIG. 2. As seen particularly in FIG. 5, the tail or lever arm 37 in its unstressed or passive state is arcuate in form. The connecting member 38 is somewhat L-shaped in that it includes a section 38a connected at substantially right angles to a section 38b. The free end of section 38a is connected to the torquing arm 36, and the free end of the section 38b is connected to the tail/lever arm 37. It will be noted that the auxiliary is devoid of any loops, but it will be understood that the wire from which the auxiliary is made will be resilient and have a memory such that when it is activated or stressed from its passive or unstressed state, it will tend to return to its passive state. Thus, the wire is of a highly resilient material such that it will not easily deform permanently when stressed. For example, the wire may be made of nickel titanium.

Depending upon whether it is desired to torque a tooth labially or lingually, the torquing auxiliary will be inserted from the gingival or the incisal. For example, the left auxiliary shown in FIG. 5 where the torquing arm 36 is inserted from the incisal will cause lingual torquing of the root of tooth 12 when the tail 37 has been properly anchored in the horizontal archwire slots of the brackets on teeth 10, 11, 13 and 15. Activating this auxiliary will involve bringing the tail/lever arm downwardly per arrow 40 and insertion in the archwire slots. Activation of the auxiliary at the right in FIG. 5 where the torquing arm has been inserted from the gingival will require bringing the tail/lever arm upwardly in the direction of the arrow 41 until the tail is anchored in the slots of the brackets on teeth 11, 10, 12 and 14, and will result in torquing the root of tooth 13 labially. It will also be appreciated that the very ends of the torquing arms may be bent over to additionally lock the auxiliary in place on the bracket of the tooth to which the torquing force will be applied.

While the tail/lever arm 37 is shown labial of the main archwire in FIGS. 1, 2 and 4 and ligated to the brackets, for purposes of better illustrating the manner in which the tail will be anchored to adjacent teeth, it will be appreciated that normally the tail will be lingual of the main archwire and therefore inserted into the archwire slots prior to insertion of the main archwire, as illustrated in FIG. 6. Then, it will be nearly impossible to see the torquing auxiliary as it will be hidden by the main archwire. In this mode, the aesthetics of the system are much improved. Further, the oral hygiene is improved inasmuch as there is less chance of having food trapped between the tail and the main archwire.

It will be appreciated that the connecting member 38 is such as to dispose the tail/lever arm along the level of the main archwire wherein the axis of torquing will be along the main archwire. Further, while the length of the tail/lever arm is such as to engage the plurality of brackets on adjacent teeth, it will be appreciated that it need only be of a length to engage one adjacent bracket if so desired.

If desired, the torquing arm 36 may be bent at a different angle to the connecting member section 38b to obtain some uprighting force or to maintain axial inclination. Further, it will be appreciated that the wire for the auxiliary may be 0.014 or 0.016 inches, or any other size, depending upon the amount of force desired.

From the foregoing, it will be appreciated that an improved torquing auxiliary is provided for torquing of a single tooth where the auxiliary is simply constructed and is devoid of any coils or loops, and further that it is easy to install and will provide better oral hygiene and improved aesthetics. Additionally, it is less bulky to use with edgewise brackets. Additionally, one form of the auxiliary is useful for providing lingual or labial root torquing.

It will be understood that modifications and variations may be effected without departing from the scope of the novel concepts of the present invention, but it is understood that this application is to be limited only by the scope of the appended claims.

I claim:

1. An individual torquing auxiliary for torquing the root of a single tooth either labially or lingually and used in combination with a main archwire, said auxiliary being a wire of highly resilient material such that it will not easily deform permanently when stressed from its passive or unstressed state and when stressed will tend to return to its passive state, said auxiliary having a torquing arm adapted to be received in a vertical slot of a bracket on the tooth to be torqued, a tail/lever arm received within a horizontally open archwire slot of a bracket on an adjacent tooth, and connecting means between the torquing arm and the tail/lever arm.

2. The auxiliary of claim 1, wherein said tail/lever arm is disposed at the level of the archwire slot and the axis of torquing is centered along the main archwire.

3. The auxiliary of claim 2, wherein said connecting means is generally L-shaped to dispose the tail/lever arm at the level of the archwire slot.

4. The auxiliary of claim 1, wherein said torquing arm is a substantially straight section and said tail/lever arm is an arcuate section in unstressed state.

5. The auxiliary of claim 1, wherein the length of the tail/lever arm is such as to at least extend substantially through the archwire slot of the adjacent bracket.

6. The auxiliary of claim 1, wherein the length of the tail/lever ar is such as to extend substantially through the archwire slots of a plurality of brackets.

7. The auxiliary of claim 1, wherein the length of the torquing arm is such as to substantially extend through the vertical slot.

8. The auxiliary of claim 1, wherein the length of the torquing arm is such as to extend through the vertical slot and be bendable over the bracket body on the tooth to be torqued.

9. The auxiliary of claim 1, wherein the tail/lever arm is first inserted in the horizontal slot and followed by the insertion of the main archwire.

10. The auxiliary of claim 1, wherein the tail/lever arm is inserted in the horizontal slot after first inserting the main archwire.

11. A torquing auxiliary for use in an edgewise bracket having a vertical slot mounted on one tooth and a bracket having a horizontally extending and labially opening archwire slot and mounted on an adjacent tooth for torquing a single tooth and used in combination with a main archwire, said auxiliary comprising a wire of highly resilient material such that it will not easily deform permanently when stressed from its passive or unstressed state and when stressed will tend to return to its passive state, said wire being sized smaller than said archwire slot, and including a torquing arm receivable in said vertical slot and a tail/lever arm, said tail/lever arm being connected to said torquing arm and being arcuate in unstressed state and received within the archwire slot of the bracket on the adjacent tooth, whereby the auxiliary will torque the root of a single tooth labially or lingually depending on the direction of insertion of the torquing arm into the vertical slot.

12. In combination with an orthodontic system for an arch of a person including a plurality of edgewise brackets mounted on the tooth of the arch and having generally aligned horizontally extending and labially opening archwise slots and at least one of the brackets having a vertical slot and a main archwire received and retained in said archwire slots, an individual torquing auxiliary for torquing the root of a single tooth either labially or lingually, said auxiliary being a wire of highly resilient material such that it will not easily deform permanently when stressed from its passive or unstressed state and when stressed will tend to return to its passive state, said auxiliary having a torquing arm adapted to be received in a vertical slot of a bracket on the tooth to be torqued, a tail/lever arm received within a horizontally open archwire slot of one or more brackets on one or more adjacent teeth and along the main archwire, and connecting means between the torquing arm and the tail/lever arm.

13. The combination of claim 12, wherein the tail/lever arm of the auxiliary is lingual to the main archwire.

14. The combination of claim 12, wherein the tail/lever arm of the auxiliary is labial to the main archwire.

15. The combination of claim 12, wherein the axis of torquing is centered along the main archwire.

16. The combination of claim 12, wherein said main archwire is round, and said auxiliary is devoid of any loops.

* * * * *

UNITED STATES PATENT AND TRADEMARK OFFICE
CERTIFICATE OF CORRECTION

PATENT NO. : 5,017,132
DATED : May 21, 1991
INVENTOR(S) : Christopher K. Kesling It is certified that error appears in the above-identified patent and that said Letters Patent is hereby corrected as shown below:

```
Col. 4, line 32, change "ar" to --arm--; and
        line 67, change "tooth" to --teeth--.
```

Signed and Sealed this

Fifteenth Day of September, 1992

Attest:

DOUGLAS B. COMER

*Attesting Officer*       *Acting Commissioner of Patents and Trademarks*